US012612592B2

(12) United States Patent
Cagnac et al.

(10) Patent No.: US 12,612,592 B2
(45) Date of Patent: Apr. 28, 2026

(54) METHOD FOR ENRICHING A BIOMASS WITH PROTEINS

(71) Applicant: FERMENTALG, Libourne (FR)

(72) Inventors: Olivier Cagnac, Libourne (FR); Axel Athane, Carbon Blanc (FR); Julien Demol, Les Billaux (FR)

(73) Assignee: FERMENTALG, Libourne (FR)

( * ) Notice: Subject to any disclaimer, the term of this patent is extended or adjusted under 35 U.S.C. 154(b) by 0 days.

(21) Appl. No.: 17/273,678

(22) PCT Filed: Sep. 5, 2019

(86) PCT No.: PCT/EP2019/073690
§ 371 (c)(1),
(2) Date: Mar. 4, 2021

(87) PCT Pub. No.: WO2020/049095
PCT Pub. Date: Mar. 12, 2020

(65) Prior Publication Data
US 2021/0340490 A1     Nov. 4, 2021

(30) Foreign Application Priority Data

Sep. 5, 2018     (FR) ...................................... 1857950

(51) Int. Cl.
| | |
|---|---|
| *C12N 1/125* | (2026.01) |
| *A23J 1/00* | (2006.01) |
| *A23L 29/281* | (2016.01) |
| *C12N 1/06* | (2006.01) |
| *C12R 1/89* | (2006.01) |

(52) U.S. Cl.
CPC .............. *C12N 1/125* (2021.05); *A23J 1/009* (2013.01); *A23L 29/281* (2016.08); *C12N 1/06* (2013.01); *C12R 2001/89* (2021.05)

(58) Field of Classification Search
CPC ........ C12R 2001/89; C12N 1/06; A23J 1/009; A23L 29/281
See application file for complete search history.

(56) References Cited

U.S. PATENT DOCUMENTS

| | | | |
|---|---|---|---|
| 4,427,580 A | | 1/1984 | Kinsella et al. |
| 2017/0020834 A1 | | 1/2017 | Brown et al. |

FOREIGN PATENT DOCUMENTS

| | | | | |
|---|---|---|---|---|
| WO | 2016/000194 A1 | 1/2016 | | |
| WO | 2016/009146 A1 | 1/2016 | | |
| WO | 2016/015013 A1 | 1/2016 | | |
| WO | 2016/120548 A1 | 8/2016 | | |
| WO | 2017/019125 A1 | 2/2017 | | |
| WO | 2017/050917 A1 | 3/2017 | | |
| WO | 2017/050918 A1 | 3/2017 | | |
| WO | 2017/093345 A1 | 6/2017 | | |
| WO | WO-2017132407 A1 * | 8/2017 | .............. | A23J 1/006 |

OTHER PUBLICATIONS

Graziani, G., Schiavo, S., Nicolai, M. A., Buono, S., Fogliano, V., Pinto, G., & Pollio, A. (2013). Microalgae as human food: chemical and nutritional characteristics of the thermo-acidophilic microalga Galdieria sulphuraria. Food & function, 4(1), 144-152 (Year: 2013).*
Total Solids (Dry Matter Content) (Standard Method 2540C) Revised Apr. 2009 retrieved from https://uwlab.soils.wisc.edu/wpcontent/uploads/sites/17/2015/08/DNR_Total_Solids.pdf on Feb. 7, 2022 (Year: 2009).*
Ungureanu, Nicoleta, Valentin Vladut, and Sorin-Stefan Biris. "Capitalization of wastewater-grown algae in bioethanol production." Proceedings of the 19th International Scientific Conference, Jelgava, Latvia. 2020. (Year: 2020).*
Graziani et al., "Microalgae as human food: chemical and nutritional characteristics of the thermo-acidophilic microalga Galdieria sulphuraria", Food & Function, 2013, vol. 4, pp. 144-152.

* cited by examiner

*Primary Examiner* — Robert J Yamasaki
*Assistant Examiner* — Trevor Kane
(74) *Attorney, Agent, or Firm* — BCF LLP

(57) ABSTRACT

The present invention relates to a method for protein enrichment of a biomass of red unicellular algae such as *Galdieria* and to the biomass thus obtained.

15 Claims, 1 Drawing Sheet

METHOD FOR ENRICHING A BIOMASS WITH PROTEINS

FIELD OF THE INVENTION

The present invention relates to a process for enriching a biomass of unicellular red algae such as *Galdieria* with proteins and the biomass thus obtained.

BACKGROUND ART

Several sources of plant proteins are known for use in food for human or animal consumption, directly or as dietary supplements, to provide animals and humans the amino acids necessary for their metabolism. These protein sources are intended as sources of amino acids available for the animals or humans once the food is ingested.

The best-known source of plant protein used in animal feed is soybean, generally used in the form of meal, which is the solid residue remaining after oil extraction. However, the use of soybean meal has several disadvantages associated with its origin. The meal is generally imported from countries which practice intensive soybean cultivation to the detriment of other plants that provide biodiversity. Furthermore, many countries promote the cultivation of genetically modified (GM) soybean varieties, which are found mixed with non-GM soybean in the meal, which does not help meet an increasing demand for genetically modified organism (GMO)-free food products of plant origin.

Other sources of plant proteins, in particular *Spirulina* or *Chlorella*, are known to be used as dietary supplements for humans.

*Spirulina*, like *Chlorella*, however, has the disadvantage of low productivity, which precludes high-yield fermenter cultivation. While their cultivation makes it possible to meet a local and limited demand for conventional food supplements, it does not allow to meet the objective of wider, economically-viable industrial production of a source of dietary protein the qualities of which will enable it to replace the common sources, such as soybean, in food for animal and human consumption.

Microalgae such as *Galdieria* are also studied with respect to their nutritional characteristics (Graziani & al., 2013). Protein extracts from microalgae such as *Aurantiochytrium* known to produce oils rich in polyunsaturated fatty acids are also described (WO 2017/132407, WO 2017/019125, WO 2016/015013). However, they are implemented on a defatted biomass, i.e., after the fat fraction has been extracted and eliminated from the cultivated biomass. This is also what is implemented for the recovery of *Chlorella* proteins (WO 2016/120548, WO 2016/00194).

Methods for the production of protein-rich microorganism biomasses are known, for example through the selection of strains particularly adapted to protein overexpression and/or to the implementation of cultivation methods that promote this overexpression and enrich the biomass with proteins. However, biomasses derived from genetically modified microorganisms (GMOs) are unsuitable for certain food and feed markets, including aquaculture (particularly in Europe).

There is an interest in being able to propose protein-rich, non-GMO biomass sources that meet an objective of wide, economically-viable industrial production as an alternative to conventional protein sources such as soybean.

DISCLOSURE OF THE INVENTION

The present invention relates to a process for producing a protein-rich biomass, the process comprising the steps of b.1. suspending a biomass of lysed microorganisms,
  b.2. acidifying the suspension to a pH less than or equal to 5,
  c. recovering the lysed biomass fraction insoluble at pH less than or equal to 5, and if need be, repeating steps b.1., b.2. and c. on the lysed biomass fraction insoluble at pH less than or equal to 5 recovered in c.
  The biomass fraction recovered in c. can then be dried.

The invention also relates to the biomass thus obtained, the use thereof for food for human or animal consumption, and to the foods and food compositions containing same.

DETAILED DESCRIPTION OF THE INVENTION

Figure 1:
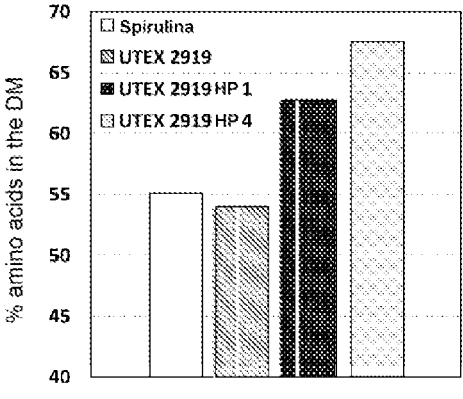
FIG. 1 represents the protein content (% amino acids in the Dry Matter) for a *Spirulina* biomass and for a of *Galdieria sulphuraria* strain UTEX 2919 biomass before and after treatment according to the invention for 1 cycle (HP1) or 4 cycles (HP4) of treatment.

The present invention relates to a process for producing a protein-rich biomass of lysed microorganisms, the process comprising the steps of
  b.1. suspending a biomass of lysed microorganisms,
  b.2. acidifying the suspension to a pH less than or equal to 5
  c. recovering the lysed biomass fraction insoluble at pH less than or equal to 5, and if need be, repeating steps b.1., b.2. and c. on the lysed biomass fraction insoluble at pH less than or equal to 5 recovered in c.

According to the invention, microorganisms are essentially microorganisms that accumulate water-soluble glycogen, such as yeasts or protists that accumulate water-soluble glycogen during their growth, in particular under industrial conditions of fermentation culture with biomass accumulation.

Advantageously, the process is particularly suitable for a biomass of phycobiliprotein-producing microorganisms. The process advantageously adds value to the biomass remaining after extraction of phycobiliproteins, a by-product of the production of these molecules of interest.

These microorganisms and their culture methods are well known to the person skilled in the art, in particular described in applications WO 2017/050917, WO 2017/050918 and WO 2017/093345.

Particular mention may be made of the unicellular red algae (URA). According to the invention, "URA" means Rhodophytes, in particular of the subdivision Cyanidiophytina, preferably of the class Cyanidiophyceae, in particular of the order Cyanidiales, more particularly of the families Cyanidiaceae or Galdieriaceae, even more particularly of the genera *Cyanidioschyzon, Cyanidium* or *Galdieria*.

Preferably, the URA are selected from the species *Cyanidioschyzon merolae* 10D, *Cyanidioschyzon merolae* DBV201, *Cyanidium caldarium, Cyanidium daedalum, Cyanidium maximum, Cyanidium partitum, Cyanidium rumpens, Galdieria daedala, Galdieria maxima, Galdieria partita* or *Galdieria sulphuraria*, more preferentially from the species *Galdieria sulphuraria*.

Preferably, the process is implemented with a lysed biomass in which at least 70% of the cells are lysed, more preferentially at least 80% of cells lysed, even more preferentially 90%, even more preferentially 95%.

According to an embodiment of the invention, the process comprises a preliminary step a. of lysis of a biomass of previously cultivated microorganisms.

Step a. of lysis can be done by any means of cellular lysis known to the skilled person. Particular mention may be made of grinding or enzymatic lysis. Preferably, cell lysis is performed by grinding, this method being particularly preferred for the lysis of URA, in particular the species *Galdieria sulphuraria*.

It can thus be done while the cells are suspended in water, fermentation must or reconstituted suspension, or on a so-called "dry" biomass, i.e., separated from the fermentation medium, fresh or after drying and storage, for example after freeze-drying.

Advantageously, lysis by grinding is carried out on a biomass of "dry" cells, in particular on a biomass of fresh cells separated from the fermentation medium after culture by any separation method well known to the skilled person, in particular by filtration or by centrifugation.

According to another embodiment of the invention, lysis by grinding is carried out on a biomass of cells previously lyophilized or dried for their storage.

Step b.1. of suspension makes it possible to obtain a suspension of the lysed biomass.

The suspension obtained in step b1 generally has between 1% and 40% dry matter, or more. Preferably it will have between 20% and 30% dry matter.

Step b.2. is carried out by adding an acid to obtain a suspension the aqueous phase of which has a pH less than or equal to 5. Preferably, a pH less than or equal to 4 will be sought.

The adjustment of the pH is done by adding an acid, mineral or organic, strong or weak, in the form of a solid or a solution, the amount of acid added being determined by the pH of the suspension to be treated and the pH value that the skilled person will try to obtain. Among the mineral acids well known to the skilled person, particular mention may be made of hydrochloric acid, sulfuric acid and phosphoric acid. Among the organic acids well known to the skilled person, particular mention may be made of acetic acid, citric acid, tartaric acid, lactic acid, preferably citric acid. Mention may also be made of acidic polyphenols such as rosmarinic acid, tannic acid, digallic acid, quercitannic acid, gallotannic acid, acidic tannins such as quercetin, ellagitannins, castalagin, castalin, casuariticin, grandinin, punicaligin punicalin, roburin A, tellimagrandin II, terflavin B, vescaligin, pendunculagin, casuariin, castlin, vescalin, preferably tannic acid. Preferably, the acids used are acids authorized for food use, in particular phosphoric acid, sulfuric acid, citric acid or tannic acid.

The acid suspension obtained by step b.2. preferably has a dry matter content greater than or equal to 1%, advantageously more than 2% dry matter, preferentially from 3 to 30% dry matter, more preferably from 4 to 15% dry matter, even more preferentially from 5 to 12%, even more preferentially from 6 to 10%.

According to a particular embodiment of the invention, steps b.1. and b.2. are consecutive, step b.2 being carried out directly after step b.1 without any other step of treatment of the biomass such as a defatting step, for example. Suspension, or dilution of the suspension is followed by the addition of acid, in solid or liquid form.

According to another particular embodiment of the invention, steps b.1. and b.2. are carried out simultaneously by adding an appropriate amount of an acid solution to obtain both the desired pH less than or equal to 5 and the desired dry matter content.

Depending on the lysed biomass recovered from step a., in particular whether the lysis was carried out on a cellular suspension in water or on a so-called "dry" biomass, the skilled person will know how to add the amounts of water and acid necessary to obtain a suspension with the desired dry matter content and the desired pH, whether these additions are made in two steps or in a single step.

Step c. is carried out by any means of separation known to the skilled person to separate the solid residues of cell lysis from the aqueous solution from the acid suspension comprising the lysed cells, in particular by filtration or by centrifugation. For filtration, particular mention may be made of tangential filtration, for example tangential filtration on ceramic membranes or organic membranes such as hollow polyethersulfone fibers. Frontal filtration can also be used (plate filter or press filter).

If need be, the suspension/acidification/recovery cycle (b.1./b.2./c.) may be repeated several times on the lysed biomass fraction insoluble at pH less than or equal to 5 recovered in c. so as to deplete it of elements soluble at acidic pH. Advantageously, the suspension/acidification/recovery cycle is repeated 1, 2 or 3 times on the lysed biomass recovered in c.

The protein-enriched biomass fraction recovered in c. can then be dried by any known drying method.

The mother liquors of the suspension are generally recovered for treatment to extract components soluble at acidic pH that can have value on their own. This is particularly the case for phycocyanins when the microorganisms are phycobiliprotein-producing microorganisms as defined above. Such a process is in particular described in patent application PCT/EP2018/058294 filed on 30 Mar. 2018.

The biomass obtained generally has at least 60% proteins (evaluated by the total nitrogen determination, N*6.25) in relation to the dry matter, preferably more than 65%, even more preferentially more than 68%, more than 70% or even more than 80%.

The biomass also preferably has a total sugar content of less than 20% in relation to the dry matter, more preferentially less than 10%, less than 5%.

The biomass obtained also preferably has a glycogen content of less than 10% in relation to the dry matter, more preferentially less than 5%, or even less than 1%, even more preferentially less than 0.1%.

Depending on the microorganisms used, the lysed biomass insoluble at pH less than or equal to 5, may have a fat content, in particular lipids, which can be at least 5%, or even at least 10% in relation to the dry matter, or even at least 15%, at least 16%, up to 20%. The fat composition will also depend on the microorganisms. For URA, the lysed biomass according to the invention generally comprises polyunsaturated fatty acids of the omega 3, 6 and 9 type, in particular oleic, palmitic and alpha-linolenic acids, which represent at least 30% of the fat, preferentially 40%, even more preferentially 50% of the fat.

The skilled person will know how to adapt the conditions of implementation of the process according to the invention, in particular the pH of the suspension and the number of suspension/acidification/recovery cycles to be repeated on the recovered lysed biomass in order to obtain a biomass with the desired amounts of proteins, sugars, glycogen and lipids and in particular as defined above.

The percentages by weight of proteins can be expressed both in relation to the proteins themselves and in relation to the amino acids contained in said proteins. According to the present invention, protein means any protein, peptide or amino acid insoluble at an acidic pH less than or equal to 5.

The present invention also relates to the biomass as previously defined, obtainable by the process according to the invention.

This biomass has advantageously:

at least 60% proteins, preferably more than 65%, even more preferentially more than 68%, more than 70% or even more than 80%, less than 20% total sugars, preferentially less than 10%, more preferentially less than 5%, less than 10% glycogen, preferably less than 5%, more preferentially less than 1% and even more preferentially less than 0.1%, and up to 20% fat, the percentages being expressed in relation to the dry matter of the biomass.

The invention also relates to the use of a biomass as described above in the fields of cosmetics, pharmaceuticals, foods for human or animal consumption.

It relates in particular to the use of a protein-enriched biomass according to the invention, as described above and below, for improving animal performance. This improvement in performance can be evaluated, in particular, by measuring feed intake, weight gain, or the feed conversion ratio.

A distinction can be made in animal feed between the feeding of livestock, particularly in industrial farming, and that of domestic animals or pets or so-called "leisure" animals, such as aquarium fish or aviary or cage birds or exotic pets.

"Livestock" means in particular grazing animals (in particular cattle raised for meat, milk, cheese and leather; sheep raised for meat, wool and cheese; goats), pigs, rabbits, poultry (chickens, hens, turkeys, ducks, geese and others), equids (ponies, horses, foals), intended to support human activities (transport, recreation) or their feeding, aquatic animals (for example fish, shrimp, shellfish (particularly oysters and mussels)). However, a distinction can be made between the feeding of fish up to the fry stage and that of farmed fish, including the feed and feed compositions intended for them.

They are to be distinguished from domestic animals, pets or leisure pets which also include mammals, ruminants or not, birds or fish. In particular, they include dogs and cats.

The invention also relates to a food, or food composition, for humans or animals, comprising a biomass according to the invention as described above. "Food" means any composition that can be used to feed humans or animals.

According to the invention the food may comprise only biomass, dried or not, processed or not, or biomass, dried or not, processed or not, mixed with any other additive, vehicle or carrier, used in the field of food for human or animal consumption, such as food preservatives, dyes, taste enhancers, pH regulators, or pharmaceutical additives such as growth hormones, antibiotics.

The present invention relates in particular to feed for animals and more particularly for livestock. These feeds are usually in the form of flours, granules or soup in which the biomass according to the invention is incorporated. "Animal feed" means anything that can be used for feeding animals.

For intensive animal farming, feeds may comprise, in addition to algal biomass, a nutritional base and nutritional additives. The bulk of the animal's feed ration thus consists of the "nutritional base" and the algal biomass. By way of example, this base is constituted by a mixture of cereals, proteins and fats of animal and/or vegetable origin.

The nutritional bases for animals are adapted to the feeding of these animals and are well known to the skilled person. In the context of the present invention, these nutritional bases include, for example, corn, wheat, pea and soybean. These nutritional bases are adapted to the needs of the different animal species for which they are intended. These nutritional bases may already contain nutritional additives such as vitamins, mineral salts and amino acids.

Additives used in animal feed can be added to improve certain characteristics of the feeds, for example to enhance the taste, to make feed materials more digestible or to protect the animals. They are frequently used in large-scale intensive livestock farming.

Additives used in animal feed are divided, in particular, into the following sub-categories (source EFSA):

technological additives: for example, preservatives, antioxidants, emulsifiers, stabilizers, acidity regulators and silage additives;

sensory additives: for example, flavorings, dyes, nutritional additives: for example, vitamins, amino acids and trace elements;

zootechnical additives: for example, digestibility enhancers, gut flora stabilizers;

coccidiostats and histomonostats (antiparasitics).

In an embodiment, the invention relates to livestock feed comprising between 1 and 60%, preferably between 1 and 20%, most preferentially between 3 and 8% of a dried biomass obtained by the process according to the invention.

In another embodiment, the invention relates to livestock feed comprising between 1 and 40%, preferably between 5 and 10% of an undried biomass obtained by the process of the invention.

According to a particular embodiment of the invention, the feed is intended for livestock, in particular cattle, sheep, pigs, rabbits, poultry and equids.

According to another particular mode of the invention, the food is intended for aquatic animals, in particular fish, at least up to the fry stage, including farmed and ornamental fish.

According to another particular embodiment of the invention, the food is intended for domestic animals, pets and/or leisure animals and exotic pets.

Finally, according to another embodiment of the invention, the food composition is intended for humans.

The invention also relates to a cosmetic, nutraceutical or pharmaceutical composition for humans or animals comprising a biomass according to the invention as described above.

According to the invention, the cosmetic, nutraceutical or pharmaceutical composition may comprise only biomass, dried or not, transformed or not, or biomass, dried or not, transformed or not, mixed with any other additive, vehicle or carrier, used in the field of cosmetics or pharmacy such as for example preservatives, dyes, pH regulators.

The invention also relates to the use of the biomass as described above in therapy, as well as in the prevention and treatment of malnutrition.

Examples

Materials and Methods

Lysed Biomass

The biomasses treated by the process according to the invention are biomasses of *Spirulina* (*Arthrospira platensis*)

and of *Galdieria sulphuraria* strain UTEX 2919 (UTEX Culture Collection of Algae, 205 W. 24th St, Biological Labs 218, The University of Texas at Austin (A6700), Austin, TX 78712 USA) cultivated according to the usual methods for cultivating these strains.

The lysed biomass has a lysed cell content of 95%

The dry matter content is 10%

Operating Procedure

The enrichment process is carried out by repeatedly rinsing the ground biomass pellet under acidic pH conditions. To do this, the operation involves the use of a centrifuge, here described by the use of a SORVALL™ RCSB plus and a Sorvall™ SLA 3000 fixed-angle rotor. The ground biomass is centrifuged at 12000×g for 15 min to pellet the insoluble fraction to the maximum. The "soluble fraction" supernatant is removed and replaced by water. The pellet is resuspended before repeating the centrifugation operation, and the pH is monitored and adjusted if necessary to a value below pH 4.8. This process, repeated 3 to 4 times, maximizes the protein and lipid enrichment of the insoluble fraction.

Analyses

Total proteins are estimated using the Kjeldahl method known to the skilled person. The amino acid profile by acid hydrolysis is carried out according to the ISO 13903:2005; EU 152/2009 method. The analysis of the lipid content and of the composition is done by GC/FID and internal calibration known to the skilled person. The sugar profile is determined by ion chromatography—pulsed amperometric detection.

Results

We monitored the composition of the heavy phase (HP or insoluble fraction) after the first extraction (HP1) and the fourth (HP4) and compared it to that of the input lysate for a *Galdieria sulphuraria* strain UTEX 2919 biomass (Table 1) and for a *Spirulina* biomass (Table 2). The percentages are expressed in relation to the Dry Matter (DM).

TABLE 1

|  | C_PC | APC | Total sugars | Proteins N*6.25 | Amino Acids | Lipids |
|---|---|---|---|---|---|---|
| UTEX 2919 | 8.3% | 0.99% | 27.5% | 58.8% | 54% | 6.5% |
| UTEX 2919 HP1 | 5.2% | 0.9% | 14% | 68.3% | 62.7% | 15% |
| UTEX 2919 HP4 | 1.9% | 0.3% | 11.3% | 73% | 68.3% | 16.1% |

A clear increase in the protein content of the lysed biomass is observed from the first suspension/acidification/recovery cycle (more than 6%). This increase is even more marked after the fourth treatment cycle (more than 16%).

TABLE 2

|  | C_PC | APC | Total sugars | Proteins N*6.25 |
|---|---|---|---|---|
| *Spirulina* | 9.3% | 2.8% | 11.75% | 68% |
| *Spirulina* HP4 (pH 4) | 5.3% | 1.2% | 13.8% | 64.32% |

Contrary to URA such as *Galdieria*, the implementation of the process on *Spirulina* leads to a decrease in the protein content in the lysed biomass insoluble at pH less than or equal to 5 (Table 2). For an extraction at pH 4, pH lower than the pHi of the phycocyanin (C-PC) of the allophycocyanin (APC) we can observe a decrease in the amount of phycocyanin and allophycocyanin in the heavy phase. At pH 4, as C-PC and APC are not soluble in water, the losses observed in HP4 in relation to the biomass are certainly due to a degradation of part of these molecules at this pH.

Figure 2:
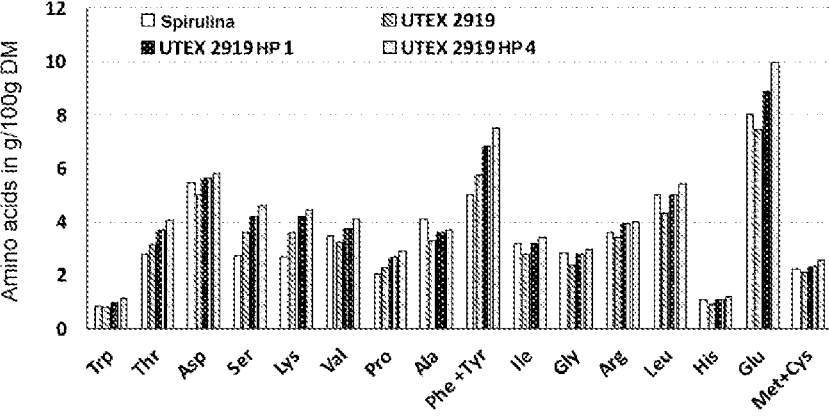
FIG. 2 represents the amino acid composition (in g/100 g DM) for a *Spirulina* biomass and for a *Galdieria sulphuraria* strain UTEX 2919 biomass before and after treatment according to the invention for 1 cycle (HP1) or 4 cycles (HP4) of treatment.

The protein content of the different biomasses is shown in FIG. 1. Looking in detail at the amino acid composition of the different products shown in FIG. 2 reveals an overall increase of all amino acids on the heavy phases, and amounts greater than or equal to those of *Spirulina* for most of them except for alanine.

If the FAO recommendations concerning essential amino acids for human nutrition are taken into account and compared with the composition of the different heavy phases, the amounts are all observed to be greater than or equal to the recommended values.

After several extractions there is still phycocyanin (C-PC and APC) left in the heavy phase which represents about 3% of the dry mass. Phycocyanin is known to be a molecule with strong antioxidant power. The fatty acid composition shows significant amounts of unsaturated fatty acids of omega 3, 6 and 9 type, in the form of polar lipids, representing more than 50% of the fat mass which represents about 5% to 20% of the dry mass of the heavy phase (Table 3).

TABLE 3

| Fatty Acids | % FA in Total Fat (FAMEs) |
|---|---|
| C8:0 Caprylic acid | 0.12 (±0.3) |
| C10:0 Capric acid | 0.17 (±0.38) |
| C12:0 Lauric Acid | 0.19 (±0.39) |
| C14:0 Myristic Acid | 0.78 (±0.58) |
| C15:0 Pentadecyl Acid | 0.27 (±0.41) |
| C16:0 Palmitic acid | 29.35 (±1.96) |
| C16:1 (n-7c) Palmitoleic acid | 0.45 (±0.46) |
| C17:0 Margaric acid | 0.15 (±0.37) |
| C18:0 Stearic acid | 4.85 (±0.95) |
| C18:1 (n-7c) Vaccenic acid | 0.36 (±0.44) |
| C18:1 (n-9c) Oleic acid ω9 | 22.34 (±1.74) |
| C18:1 (n-9t) + C18:1 (n-12t) | 0.14 (±0.37) |
| C18:2 (n-6c) Linoleic acid (LA) ω6 | 33.77 (±2.09) |
| C18:2 t2 | 0.09 (±0.34) |
| C18:3 (n-3) α-Linolenic acid (ALA) ω3 | 5.87 (±1.02) |
| C20:0 Arachidic acid | 0.19 (±0.39) |
| C20:1 (n-9c) Gondoic acid | 0.25 (±0.41) |
| C20:2 (n-6c) Eicosadienoic acid | 0.46 (±0.46) |
| C20:3 (n-3c) Eicosatrienoic acid | 0.06 (±0.33) |
| C22:0 Behenic acid | 0.07 (±0.33) |
| C24:0 Lignoceric acid | 0.06 (±0.33) |
| Ratio ω6/ω3 | 5.76 |

Sugars are below the detection limit of the method, as are fibers (Table 4).

TABLE 4

| Sugars | % DM |
|---|---|
| Glucose | <0.2 |
| Fructose | <0.2 |
| Sucrose | <0.2 |
| Lactose | <0.2 |
| Maltose | <0.2 |
| Galactose | <0.2 |
| Sum of reducing sugars | <0.2 |
| Sum of sugars (mono and disaccharides) | <0.2 |
| Fiber content | <0.5 |
| Ash content | 2.00 (±0.28) |

The process according to the invention was repeated on a *Galdieria sulphuraria* strain UTEX 2919 biomass cultivated according to the method described in patent application WO 2017/050917.

The starting biomass comprises more than 70% proteins in relation to DM. After three treatments according to the invention, a biomass with more than 80% proteins is obtained, an increase of more than 14%.

Serial extractions are performed on 3 biomasses having different glycogen contents. We can note that nearly all the soluble glycogen of the biomass is found in solution after the first extraction.

TABLE 5

| Monitoring of glycogen solubilization in the supernatant during serial extraction. | | | |
|---|---|---|---|
| SAMPLE | # 1 | # 2 | # 3 |
| Glycogen (% DM) | 12.5 | 15.2 | 21.3 |
| Proteins (% DM) | 61.6 | 56 | 54.6 |
| Supernatant 1 glycogen (g/l) | 4.03 | 5.05 | 12.3 |
| Supernatant 2 glycogen (g/l) | 0 | 0 | 0.971 |
| Supernatant 3 glycogen (g/l) | 0 | 0 | 0 |
| HP1 proteins (% DM) | 68.2 | 62.6 | 64.2 |
| HP2 proteins (% DM) | 68.6 | 63.6 | 64.2 |
| HP3 proteins (% DM) | 69.6 | 66.4 | 68.8 |

The protein-enriched heavy phase thus obtained can then be enzymatically treated with proteases to obtain a protein hydrolysate and increase the solubility and digestibility of the product.

Depending on the different periods of life and the daily energy expenditure of each person, the amount of protein recommended (ANSES, 2007) will vary. In healthy adults, the Recommended Dietary Allowance (RDA) for protein is 0.83 g/kg/day. However, these allowances vary and are increased in pregnant women, the elderly and certain athletes.

The protein-enriched fraction produced by the process described in this invention may be consumed directly in the form of a cold-pressed tablet, a powder in capsule form, or directly as a powder to be mixed with other ingredients. This fraction may also be incorporated in other food preparations which may be used in the manufacture of bread cakes, cookies or other pastries, or cereal bars, or any preparation as a substitute for conventional flour in order to enrich the food thus prepared with protein.

We can also envisage a use in preparations based on milk (animal or plant), raw or fermented milk, such as cream desserts, yoghurt, cheese. It can be added to obtain a protein-enriched milk or cheese preparation while reducing the amount of fat. It can also be envisaged to make the preparations with bases of raw cheeses, of pressed or unpressed cooked cheeses, or of processed cheeses. The algae can be incorporated into the mass or even simply outside on the crust if the latter is edible.

This protein fraction can also be incorporated into preparations for use as a meat substitute such as veggie burgers, or into surimi-style protein sticks, in which these proteins can be textured or used as is.

Another example of use would be in the form of a powder to be added in drinks such as smoothies or shakes.

Examples of Composition:

Flour Enriched with Algae Proteins:

Composition for 1 kg of flour:
  800 gr of wheat type flour (10-12% proteins)
  200 gr of protein-enriched seaweed extract (65 to 80% proteins)
  I.e., 16 to 19% proteins per 100 g of flour versus 10 to 12% for normal type 55 wheat flour.

Cookies Made with Flour Enriched with Algae Proteins

Ingredients for 100 g of cookies (7 g to 9 g of proteins):
  45 g flour enriched with seaweed protein
  23 g butter
  21.7 g sugar
  5 g cocoa powder
  4 g eggs
  1 g salt
  0.3 g baking powder
Bread Made with Flour Enriched with Algae Proteins Ingredients for 100 g of bread (10 to 25 g of proteins):
  63.2 gr flours enriched with seaweed protein
  34 g water
  1.8 g salt
  1 gram baker's yeast
Veggie Burger with Seaweed Composition for a 100 g Burger.

Water, chickpea flour (26%), seaweed powder (25%), onion, carrot, wheat gluten (3%), lemon juice, yeast extract, potato starch, vegetable oil (sunflower), turmeric, garlic, acidity regulator (potassium chloride), antioxidant, potato fiber, thickener (carrageenan), starch (corn, wheat), emulsifier (guar gum).

This represents between 22 and 33 g of protein per burger.

Dairy Product Enriched with Algae Proteins.

Preparation based on Gouda type cheese.

The protein-enriched seaweed fraction is added to the coagulated milk proteins before pressing the paste. The percentage of protein-enriched seaweed fraction can vary from 1% to 50%. In this case the limiting factor will be related to the appearance of the final product and in particular to its texture and cutability.

TABLE 6

| Main components in grams per 100 grams of product. | | | |
|---|---|---|---|
| | Protein | Lipids | Water | Carbohydrates |
| Gouda | 24 g | 29.9 g | 38.6 g | 0 g |
| Preparation containing 25% algae extract | 30 to 34 g | 22.5-26 g | 38.6 g | 2.5 g |

Powder for Beverages Enriched with Algae Proteins.

Composition for a smoothie:
  93.8 g of powder from the fraction enriched with algae protein
  5 g natural fruit flavor
  0.25 g xanthan gum
  0.2 g guar gum
  0.25 g natural sweetener or flavoring with sweetening power
  Mix 25 g of powder in 200 ml of cold water or fruit juice.

This represents between 15 and 18.5 g of proteins per drink.

Composition for a Shake:
  84.35 g of powder from the fraction enriched with algae protein
  10 g milk powder
  5 g cocoa
  0.2 g xanthan gum
  0.2 g guar gum
  0.25 g sweetener
  Mix 25 g of powder in 200 ml of cold or hot water. This represents between 15 and 20 g of proteins per drink.

REFERENCES

WO 2016/00194
WO 2016/120548

WO 2016/015013
WO 2017/019125
WO 2017/050917
WO 2017/050918
WO 2017/093345
WO 2017/050917
WO 2017/132407
US 2017-020834
Graziani & al., Food & Function, vol. 4, no 1, 2013, 144-152.

The invention claimed is:

1. A process for producing a protein-rich biomass and removing glycogen from a biomass of lysed microorganisms that accumulate water-soluble glycogen during their growth selected from unicellular red algae (URA) of the genera *Cyanidioschyzon, Cyanidium* and *Galdieria*, wherein the process comprises the steps of:

a) lysis of a biomass of microorganisms, b) suspending and acidifying the biomass of step a), wherein the suspension and the acidification consists in:

b1) suspending the biomass of lysed microorganisms obtained in step a, b2) acidifying the suspension of step b1 to a pH less than or equal to 5, wherein steps b1) and b2) are simultaneous or consecutive, when b1) and b2) are consecutive step b2) being carried out directly after step b1) without any further biomass treatment step; and wherein the acid suspension obtained in step b2) has a dry matter content from 3 to 30%, and c) recovering the lysed biomass fraction insoluble at pH less than or equal to 5, wherein the recovered lysed biomass has a glycogen content of less than 10% in relation to the dry matter, and wherein an increase of the protein content of more than 14% in the recovered lysed biomass is obtained relative to the protein content of the lysed biomass in step a);

wherein the process does not comprise a defatting step.

2. The process according to claim 1, wherein the biomass recovered in step c is dried.

3. The process according to claim 1, wherein the microorganisms are unicellular red algae (URA) of the families Cyanidiaceae or Galdieriaceae.

4. A protein-rich lysed microorganism comprising the recovered lysed biomass obtained from step c of claim 1.

5. The biomass according to claim 4, wherein the biomass comprises at least 60% proteins in relation to the dry matter, and a total sugar content equal or less than 20% in relation to the dry matter and/or a glycogen content of less than 10% in relation to the dry matter and/or a fat content of at least 5% in relation to the dry matter.

6. Food or food composition for human or animal consumption wherein the food or food composition comprises a biomass of lysed microorganisms as defined in claim 4 the recovered lysed biomass obtained from step c of claim 1.

7. The process according to claim 1, wherein the acid suspension obtained in step b2) has a pH less than or equal to 4.5.

8. The process according to claim 1, wherein the microorganisms are unicellular red algae (URA) of the species *Cyanidioschyzon merolae* 10D, *Cyanidioschyzon merolae* DBV201, *Cyanidium caldarium, Cyanidium daedalum, Cyanidium maximum, Cyanidium partitum, Cyanidium rumpens, Galdieria daedala, Galdieria maxima, Galdieria partita* or *Galdieria sulphuraria.*

9. The process according to claim 1, wherein the steps b1), b2) and c) are repeated on the lysed biomass fraction recovered in step c.

10. The process according to claim 9, wherein the steps b1), b2) and c) are repeated 1, 2 or 3 times on the lysed biomass fraction recovered in step c).

11. The process according to claim 1, wherein the said lysed biomass fraction recovered in step c) has a glycogen content of less than 5% in relation to the dry matter.

12. The process according to claim 1, wherein the said lysed biomass fraction recovered in step c) has a glycogen content of less than 1% in relation to the dry matter.

13. The process according to claim 1, wherein the said lysed biomass fraction recovered in step c) has a glycogen content of less than 0.1% in relation to the dry matter.

14. The process according to claim 1, wherein the acid suspension obtained in step b2) has a dry matter content from 4 to 15%.

15. The process according to claim 1, wherein the increase of the protein content in the recovered lysed biomass is of more than 16%.

* * * * *